US00PP34178P2

(12) United States Plant Patent
Yori

(10) Patent No.: US PP34,178 P2
(45) Date of Patent: May 3, 2022

(54) ALMOND TREE NAMED 'PY2'

(50) Latin Name: *Prunus dulcis*
Varietal Denomination: PY2

(71) Applicant: Phillip Martin Yori, Ceres, CA (US)

(72) Inventor: Phillip Martin Yori, Ceres, CA (US)

( * ) Notice: Subject to any disclaimer, the term of this patent is extended or adjusted under 35 U.S.C. 154(b) by 0 days.

(21) Appl. No.: 17/504,398

(22) Filed: Oct. 18, 2021

(51) Int. Cl.
*A01H 5/08* (2018.01)
*A01H 6/74* (2018.01)

(52) U.S. Cl.
USPC ..... Plt./155

(58) Field of Classification Search
USPC ..... Plt./155
See application file for complete search history.

(56) References Cited

U.S. PATENT DOCUMENTS

| | | | |
|---|---|---|---|
| PP2,641 | P | 6/1966 | Arakaki |
| PP3,483 | P | 2/1974 | Stretch et al. |
| PP13,286 | P2 | 11/2002 | Kester et al. |
| PP26,083 | P3 | 11/2015 | Bennett |
| PP32,301 | P2 | 10/2020 | Slaughter |

*Primary Examiner* — Susan McCormick Ewoldt
(74) *Attorney, Agent, or Firm* — Sierra IP Law, PC; Mark D. Miller

(57) ABSTRACT

The present invention provides a new and distinct variety of almond tree, named 'PY2', substantially as described and illustrated herein, which produces an improved yield, is a compatible pollinator with other varieties, and is ready for harvest at approximately the same time as other varieties. The 'PY2' variety is a good replacement for inter-planting with other varieties by providing compatible pollination, similar bloom and harvest times, and improved nut yield.

14 Drawing Sheets

Latin name: *Prunus dulcis*
Varietal denomination: 'PY2'.

BACKGROUND OF THE NEW VARIETY

The present invention relates to a new and distinct variety of almond tree, botanically know as *Prunus dulcis*, which will hereby be denominated by the cultivar name 'PY2', and more specifically to an almond tree that produces a crop for harvesting in late September and shipment in early October under the ecological conditions prevailing in the Modesto area of the San Joaquin Valley of central California.

'PY2' was discovered in 2001 as a seedling growing on the inventors property near the property line adjacent to a cultivated orchard of 'Nonpareil' (unpatented) almond trees, with a dairy farm on the other side of the property line located in Stanislaus County, Calif., in the San Joaquin Valley. The variety has been observed to have heavy nut production, as compared to the unpatented 'Nonpareil' variety. Asexual reproduction of the tree has produced progeny that are consistent with the original specimen as to vegetative characteristics.

ORIGIN AND ASEXUAL REPRODUCTION

The variety was discovered by Phillip Yori as a volunteer seedling adjacent to an orchard of 'Nonpareil' (unpatented) almond trees on his property located in Stanislaus County, Calif. The original seedling was asexually reproduced in 2001 in Stanislaus County, Calif. by collecting budwood from the mother tree that was budded onto 23 trees on unpatented 'Nemaguard' and other rootstocks. In 2005, after approximately four years of observation, during which the variety's unusually heavy yields relative to the unpatented 'Nonpareil' variety were noted, another 224 trees of the new variety were budded on unpatented 'Nemaguard' rootstock and inter-planted throughout an orchard of unpatented 'Nonpareil' almond trees and other varieties. All of these trees have survived.

Reproduction by budding and grafting resulted in true-to-type progeny with respect to all tree vegetative and reproductive characteristics. These reproductions utilized unpatented 'Nemaguard' rootstock on which the present variety was compatible and true to the original tree in all respects.

The presently observed reproduced specimens are now in their 20th leaf.

SUMMARY OF THE VARIETY

The present variety was selected and tested because of its heavy nut production and has the following outstanding and distinguishing characteristics when grown under normal horticultural practices in the Modesto area of the San Joaquin Valley of central California. The harvest date of 'PY2' approximately three weeks after that of unpatented 'Nonpareil', and near in time to that of 'Monterey' (U.S. Plant Pat. No. 3,483). Nut yield of the new 'PY2' variety is on average significantly greater than that of the unpatented 'Nonpareil' variety. The new 'PY2' variety blooms at approximately the same time as 'Monterey' (U.S. Plant Pat. No. 3,483), is a compatible pollinator with 'Monterey', and is ready for harvest at approximately the same time as 'Monterey'. The new 'PY2' variety is therefore a good replacement for unpatented 'Nonpareil' to be inter-planted in orchards with 'Monterey' (U.S. Plant Pat. No. 3,483) by providing compatible pollination, similar bloom and harvest times, and greater nut yield than unpatented 'Nonpareil'.

The present variety is a good pollinator for use with unpatented 'Dallas', 'Monterey' (U.S. Plant Pat. No. 3,483), 'Bennett-Hickman' (U.S. Plant Pat. No. 26,083), and unpatented 'Nonpareil' as well as other varieties.

DESCRIPTION OF THE PHOTOGRAPHS

The branches, nuts, foliage and flowers of the new almond variety are illustrated by the accompanying color photographs. The samples depicted in the photographs are taken from trees that are in their 20th year, grown utilizing unpatented 'Nemaguard' rootstock, under the ecological conditions prevailing in the Modesto area of the San Joaquin Valley of central California.

Figure 1:
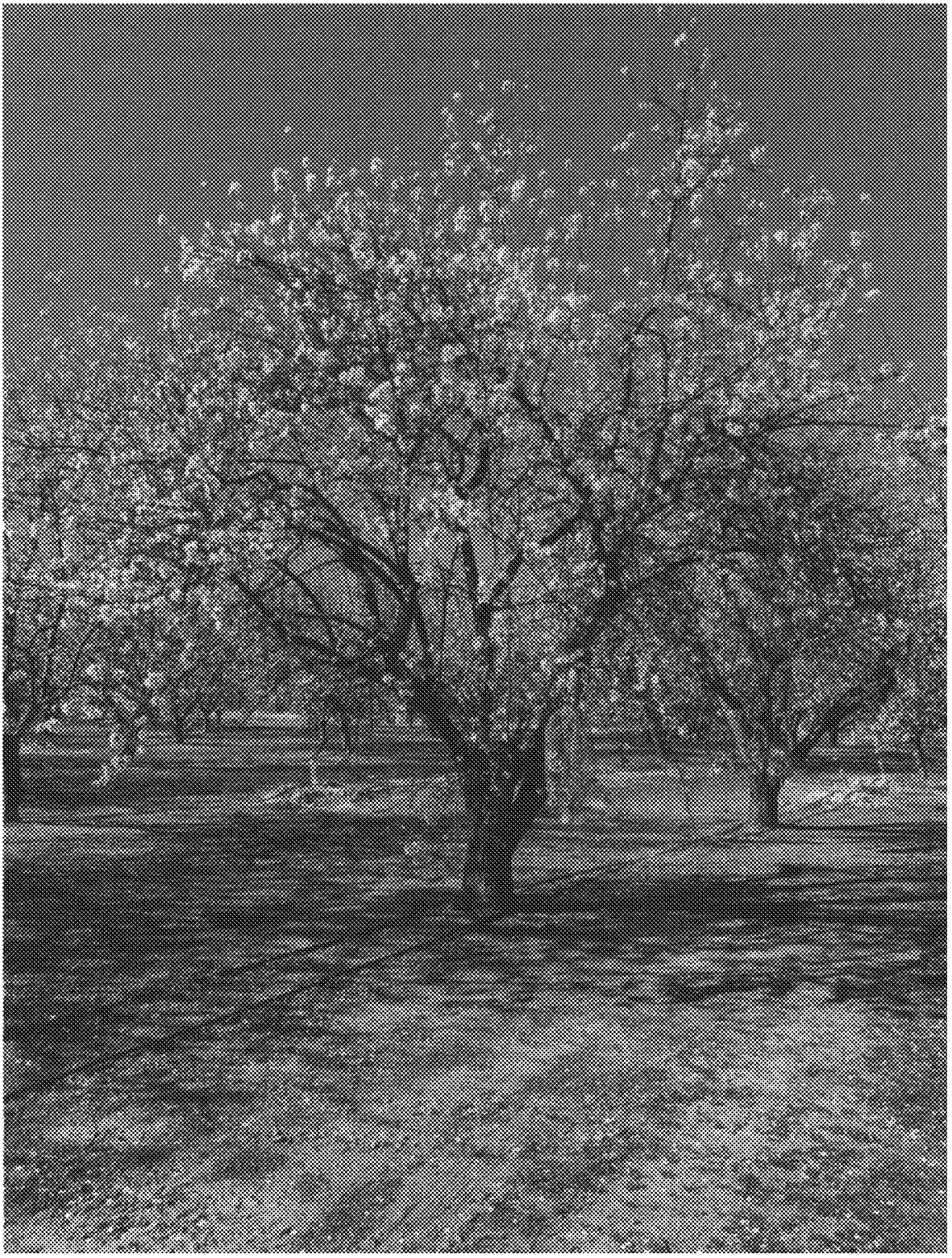
FIG. 1 is a view of a tree of the present variety in bloom in February.
Figure 2:
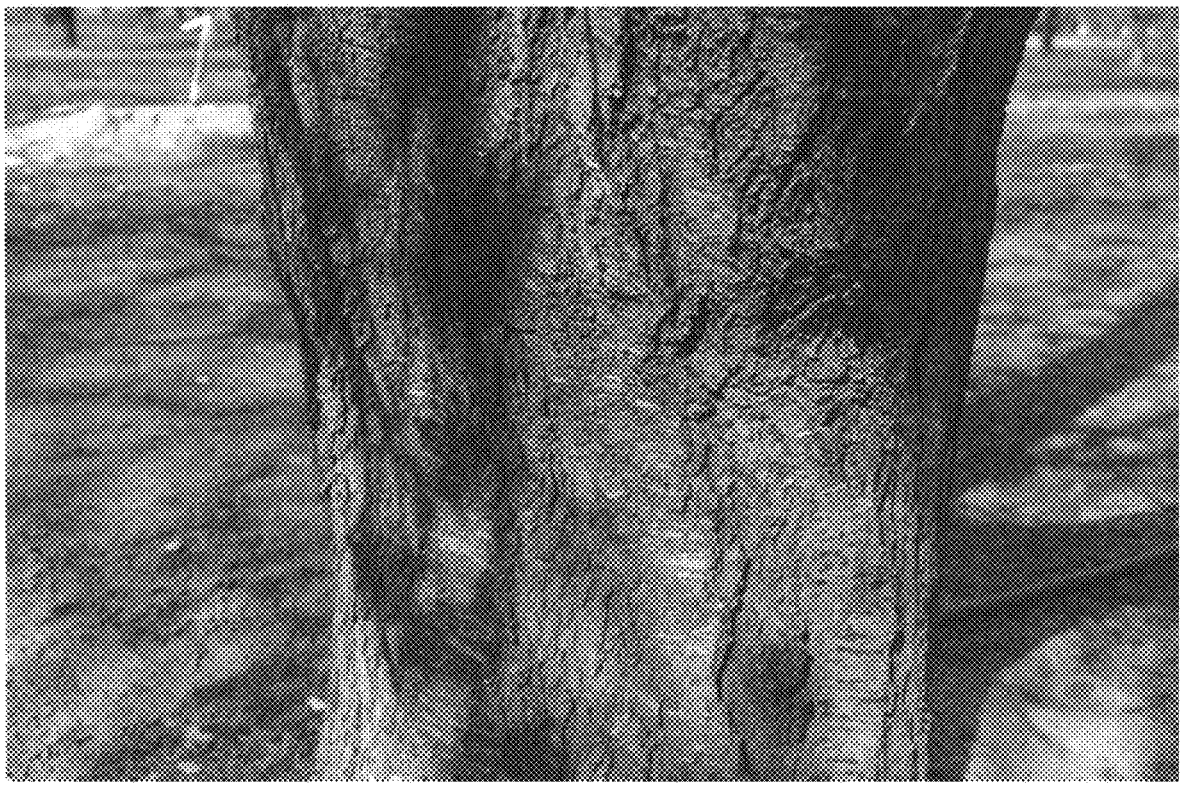
FIG. 2 is a close up view of a trunk of a tree of the new variety.
Figure 3:
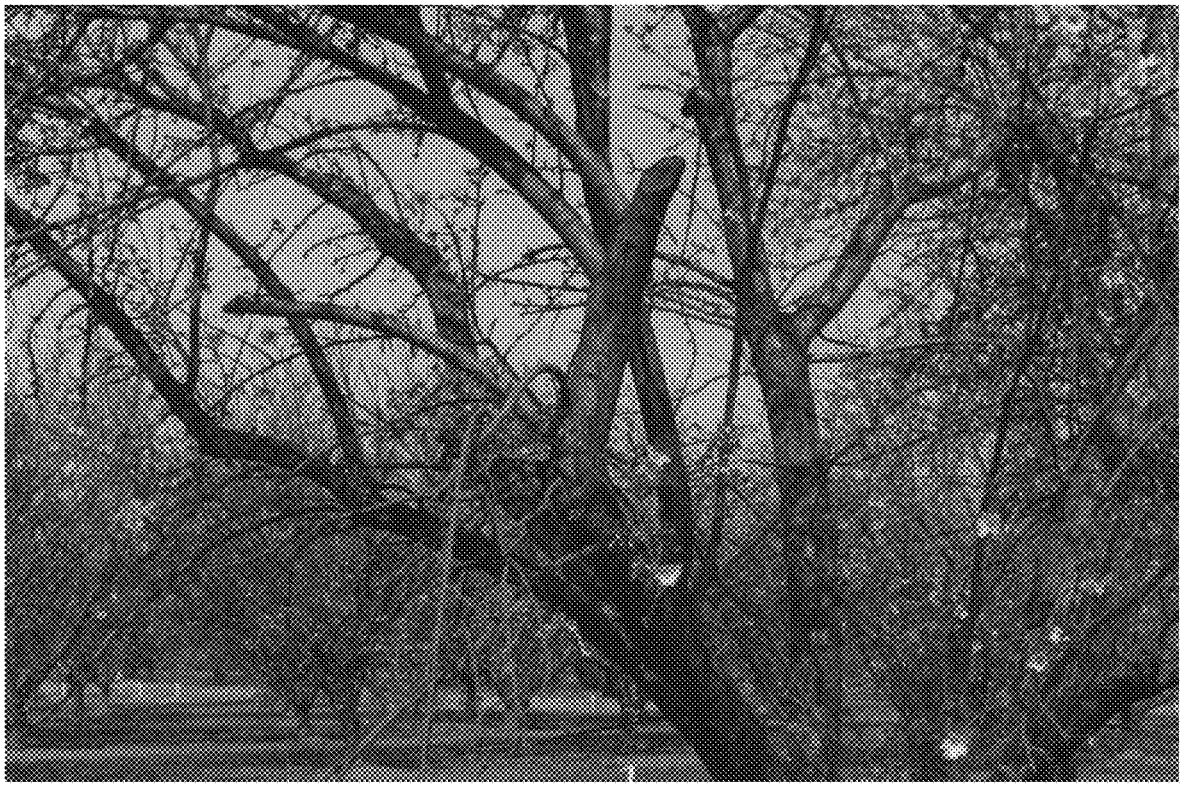
FIG. 3 is a view of branches of the present variety at bloom.
Figure 4:
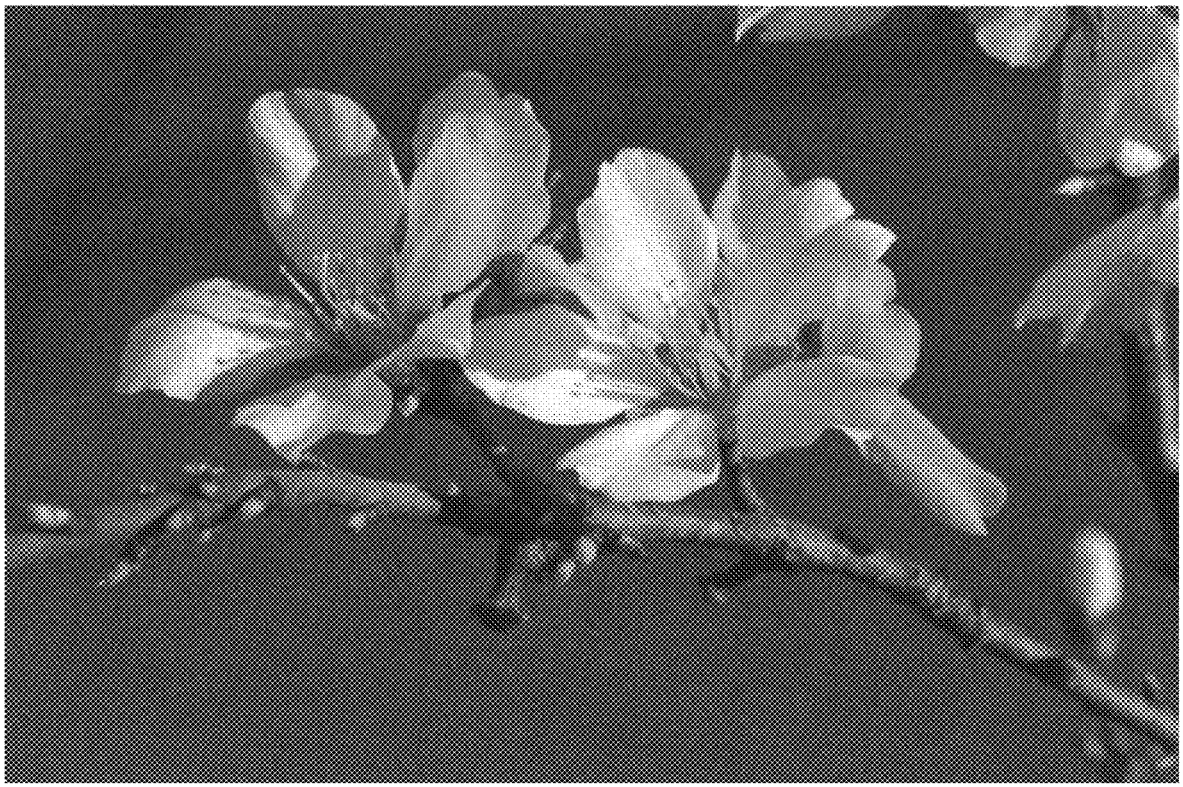
FIG. 4 is a close up view of a branch with flowers of the new variety.
Figure 5:
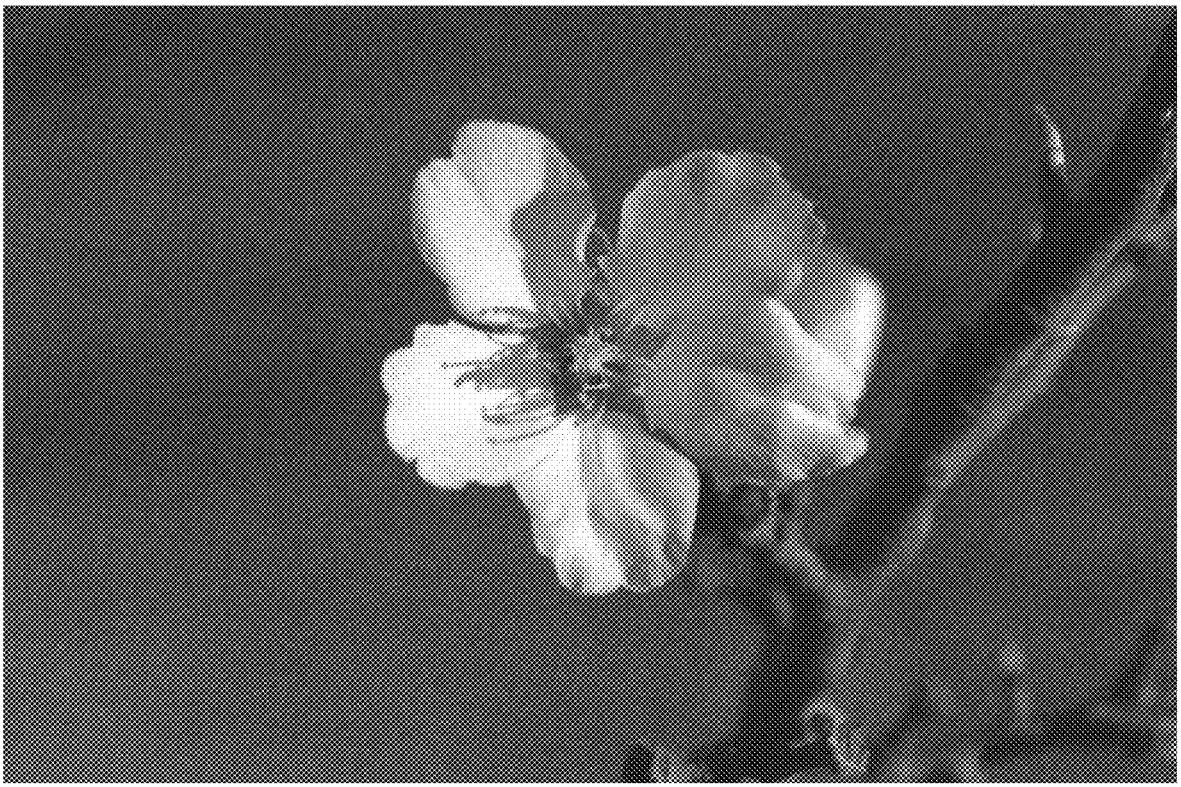
FIG. 5 is a close up view of a single flower of the new variety.
Figure 6:
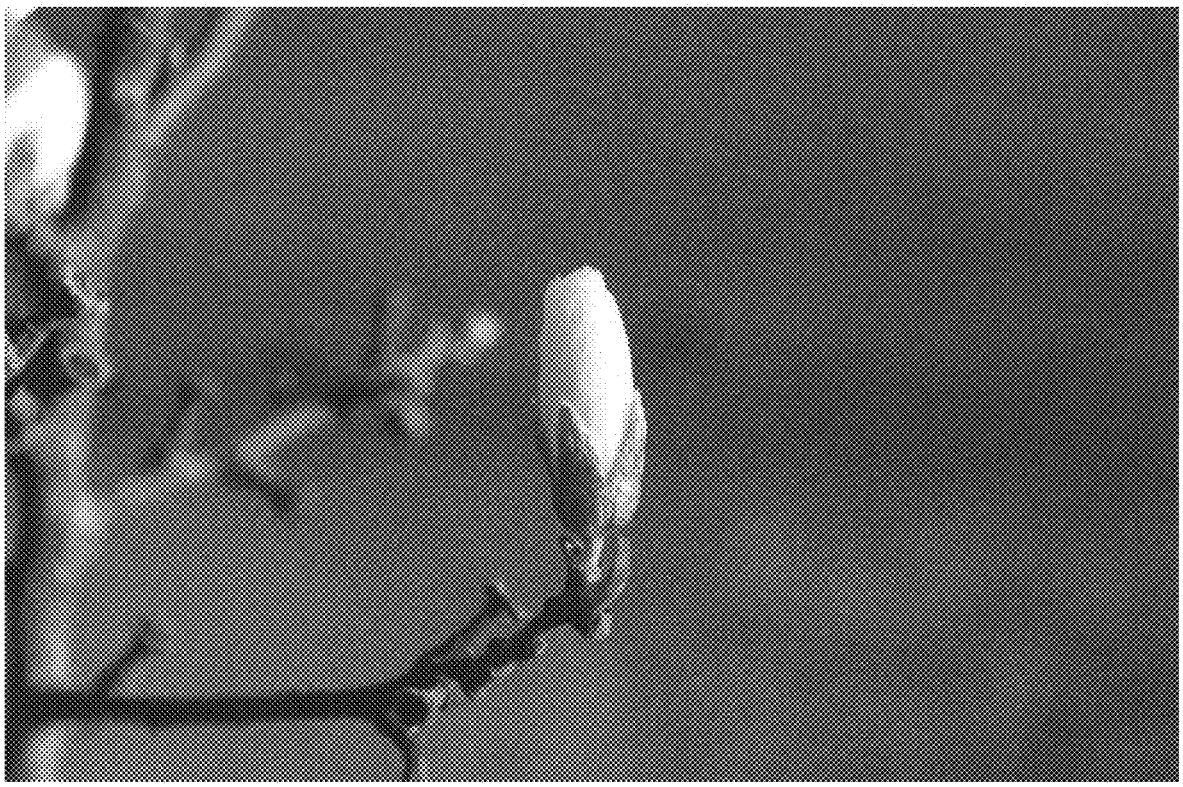
FIG. 6 is a close up view of a single flower bud of the new variety.
Figure 7:
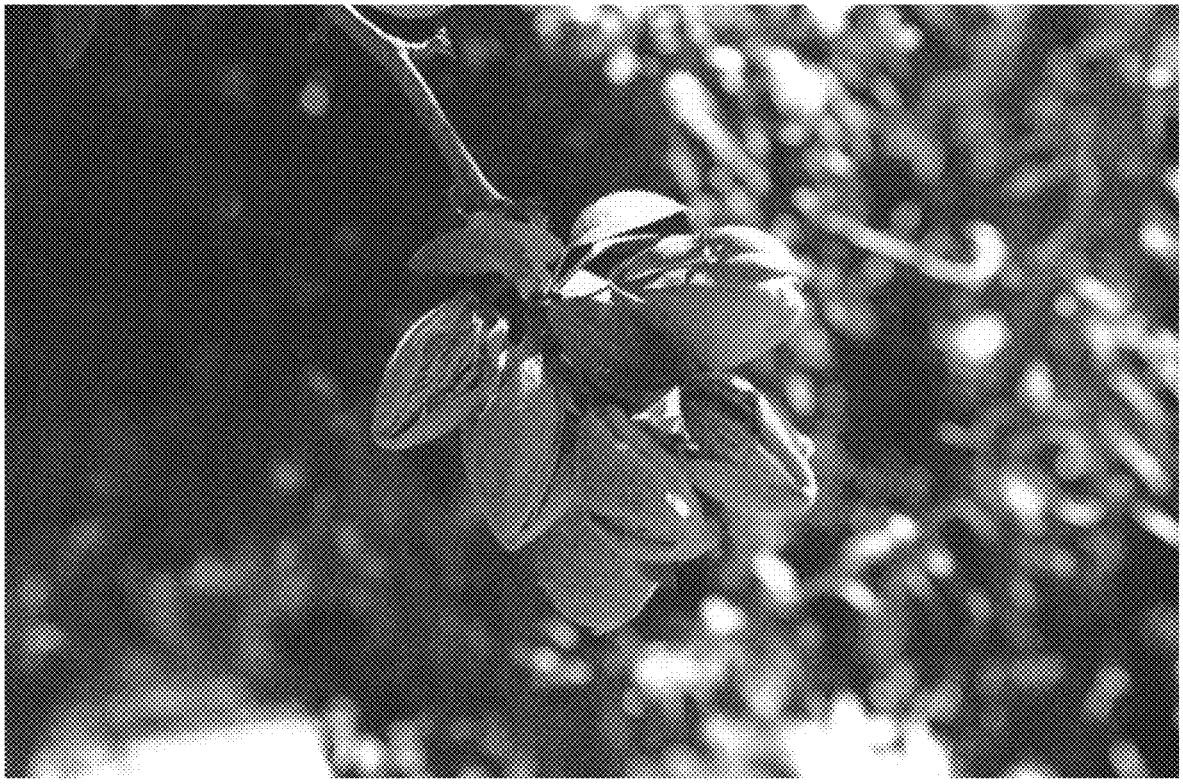
FIG. 7 is a close up view of a cluster of nuts of the new variety in situ.
Figure 8:
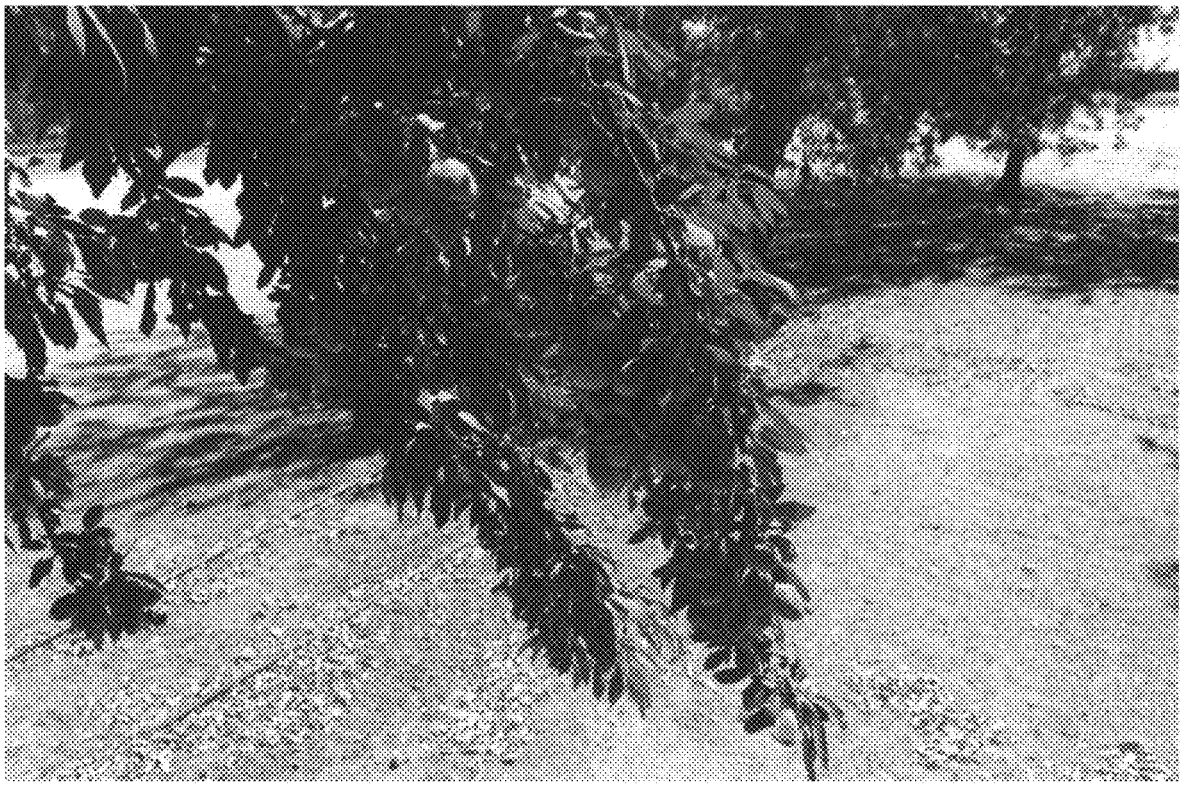
FIG. 8 is a view of mature nuts in situ on tree branches of the new variety just prior to harvest.
Figure 9:
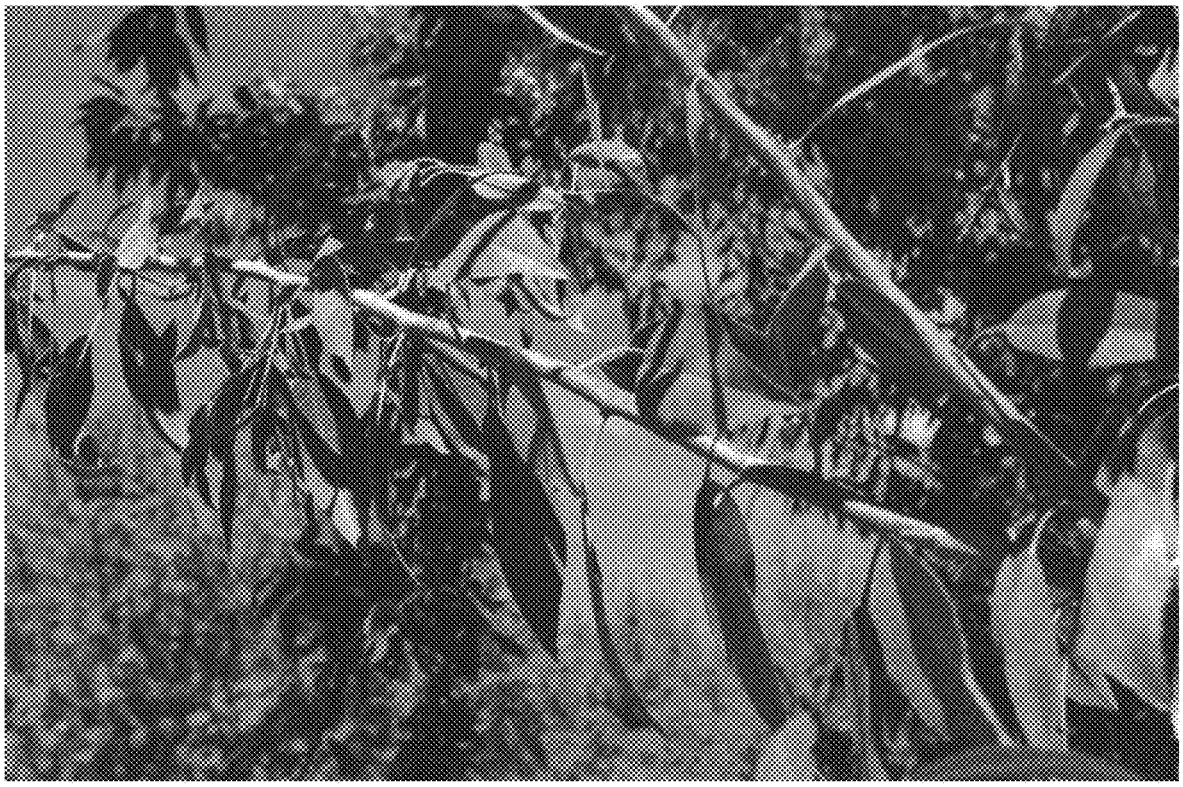
FIG. 9 is a close up top view of foliage of the new variety.
Figure 10:
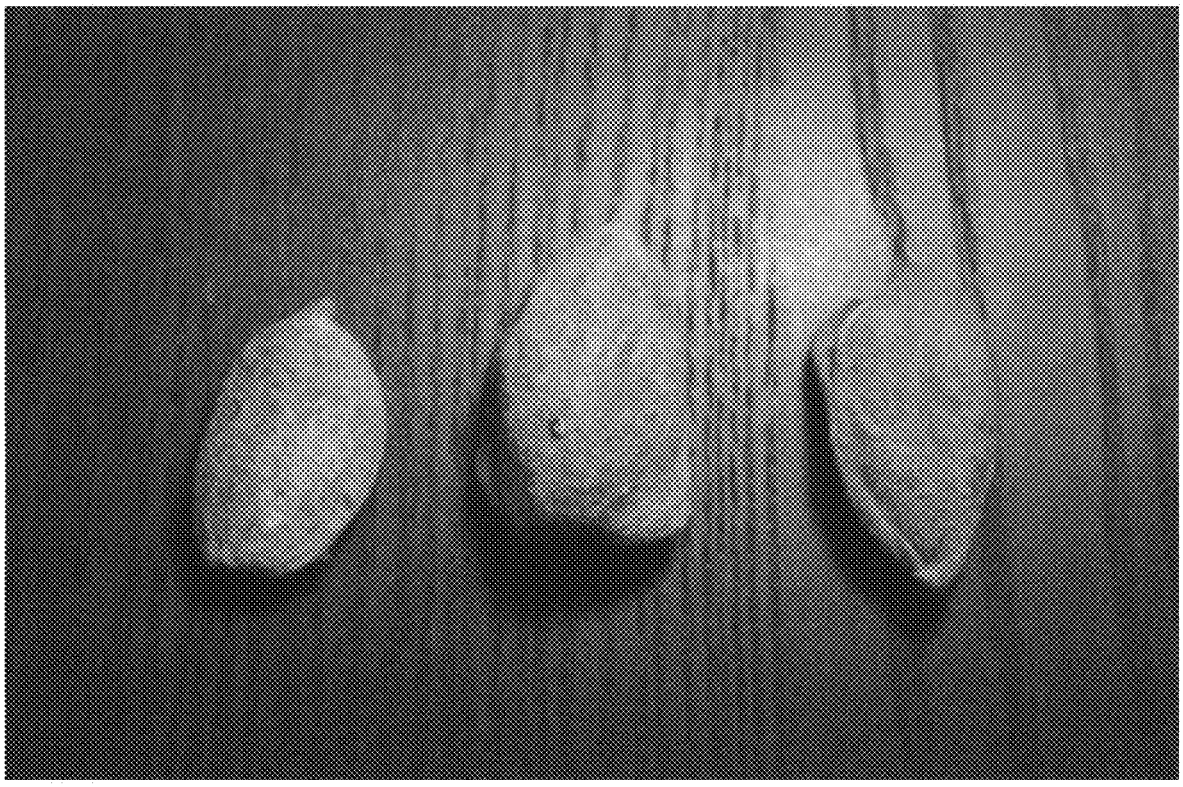
FIG. 10 is a close up view of hulls containing shells and nuts of the new variety.
Figure 11:
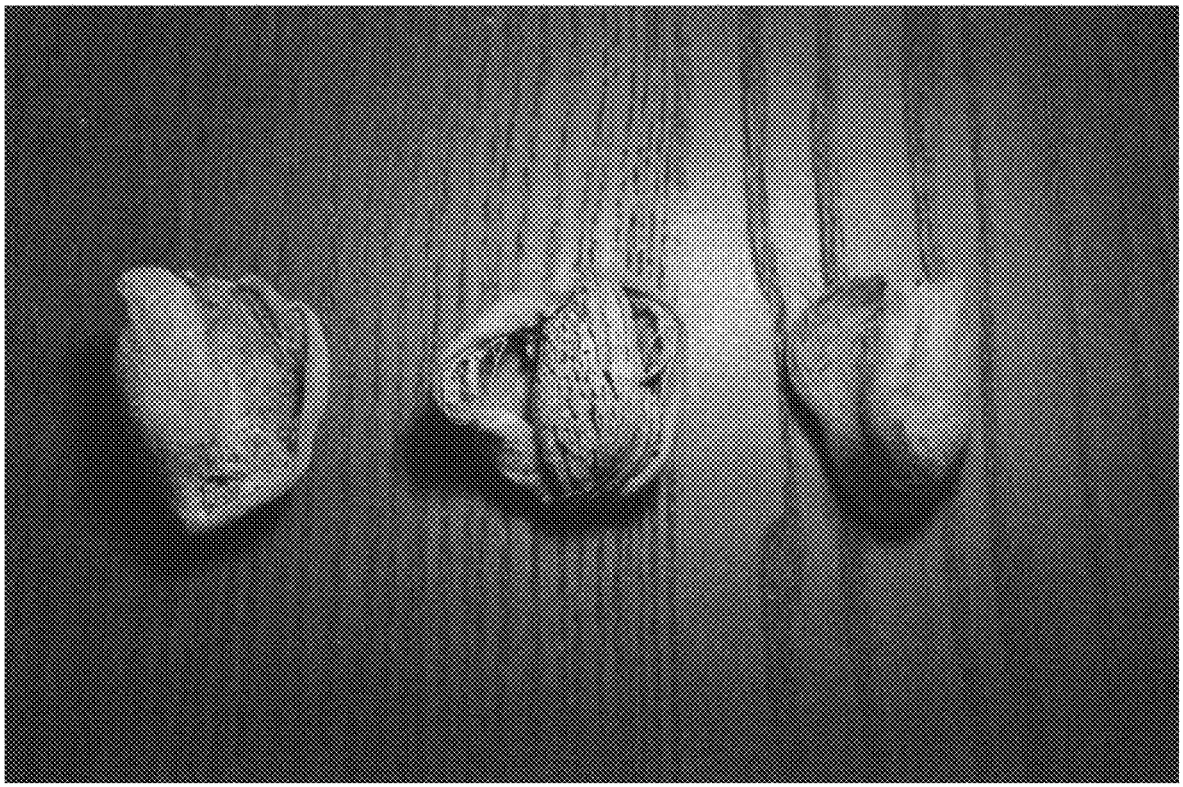
FIG. 11 is a close up view of hulls and shells of the new variety.
Figure 12:
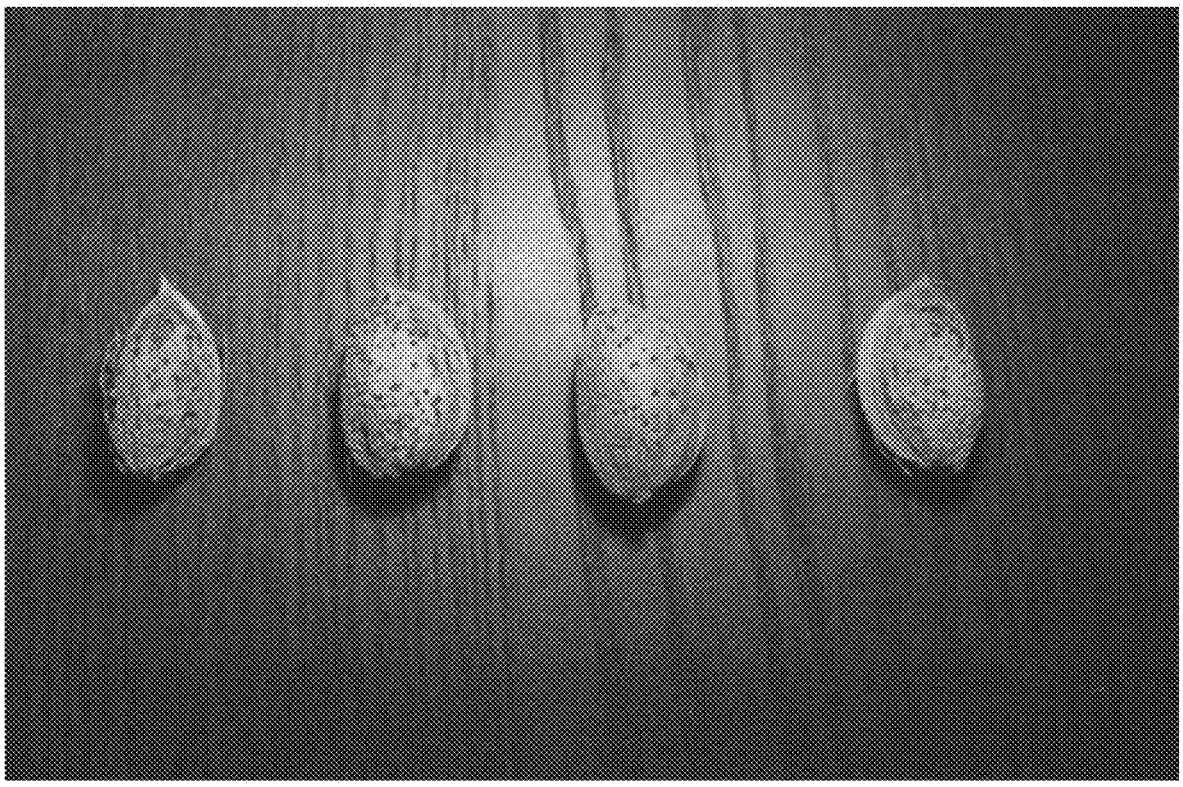
FIG. 12 is a close up view of shells of the new variety.
Figure 13:
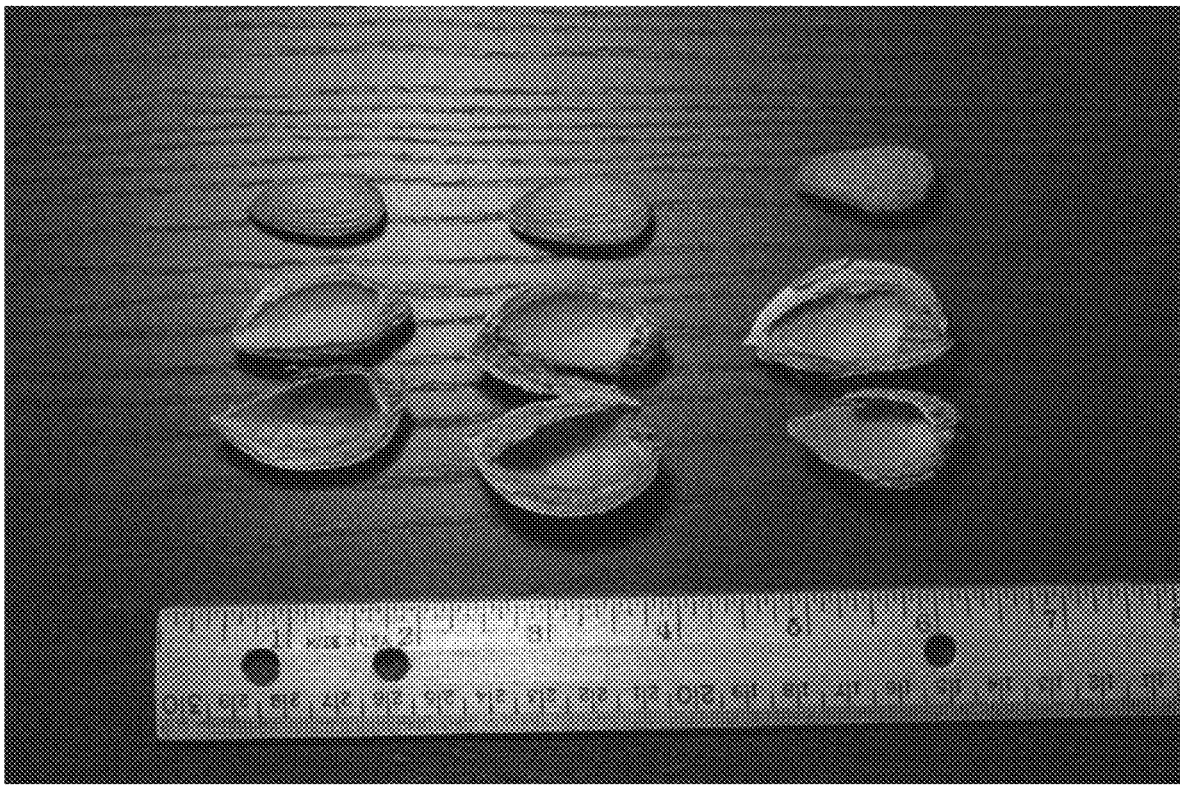
FIG. 13 is a close up view of shells of the new variety that have been open and the kernels removed.
Figure 14:
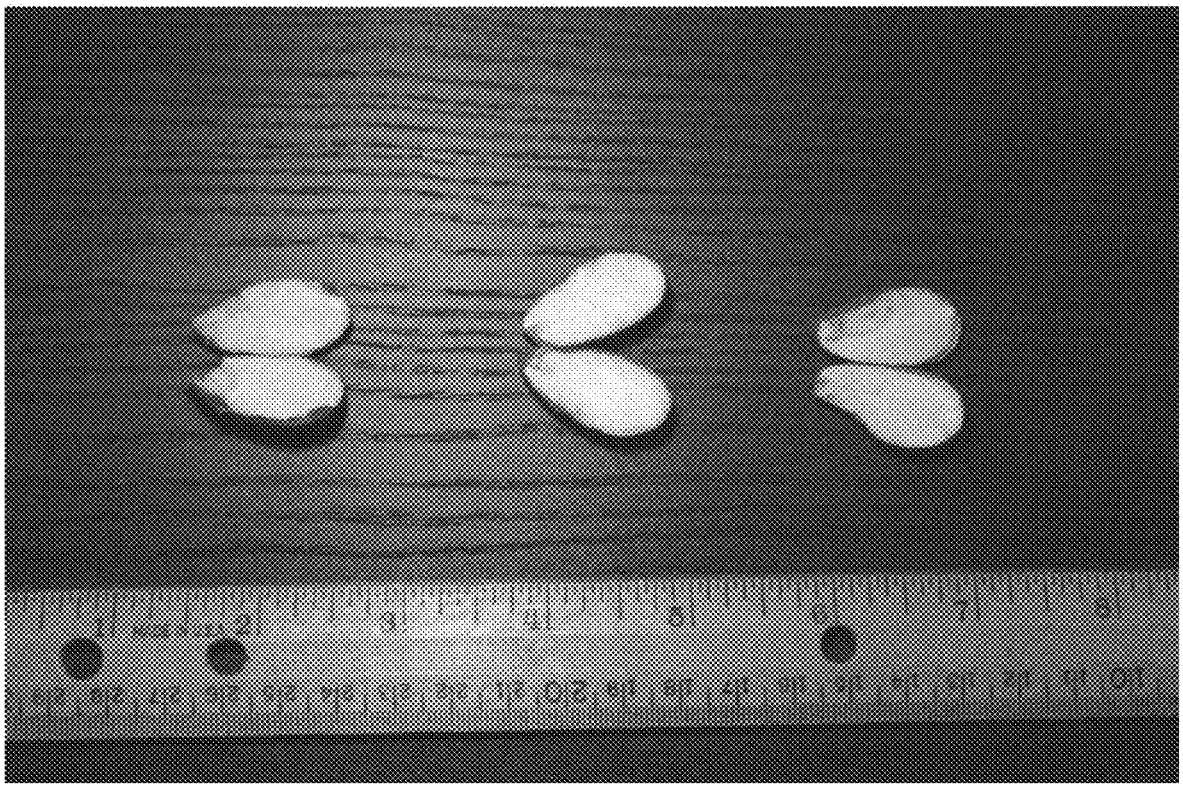
FIG. 14 is a close up view of kernels of the new variety which have been cut open.

The colors in the photographs are as true as can be reasonably obtained by conventional photographic procedures. Due to chemical development, processing and printing, the bark, leaves, nuts and flowers depicted in these photographs may, or may not, be accurate when compared to the actual specimen. For this reason, future color references should be made to the color plates and descriptions provided hereinafter.

DETAILED BOTANICAL DESCRIPTION OF THE NEW VARIETY

Referring now more specifically to the pomological characteristics of this new and distinct variety of almond tree, the following has been observed under the ecological conditions prevailing in Ceres Calif., which is near Modesto, in Stanislaus County, Calif. (San Joaquin Valley). Observations were performed at the flowering stage on Feb. 23, 2021, and just prior to the harvest stage on Sep. 18, 2021.

All major color code designations are by reference to the Dictionary of Color by Maerz & Paul, First Edition 1930. Common color names are also used.

NOT A COMMERCIAL WARRANTY

The following detailed description has been prepared to solely comply with the provisions of 35 U.S.C. § 112, and does not constitute a commercial warranty, (either expressed or implied), that the present variety will in the future display the botanical or other varietal characteristics as set forth, hereinafter. Therefore, this disclosure may not be relied upon to support any future legal claims including, hut not limited to, breach of warranty of merchantability, or fitness for any particular purpose which is directed, in whole, or in part, to the present variety.

Tree:

*Origin*.—The present variety was discovered as an open pollinated seedling of unknown parentage growing within the cultivated region adjacent to the inventor's orchard which is located in Ceres, Calif.

*Vigor*.—Considered very vigorous.

*Hardiness*.—Considered hardy under typical San Joaquin Valley climatic conditions.

*Chilling requirement*.—Considered normal under prevailing San Joaquin Valley climatic conditions.

*Tree form*.—Considered spreading and upright in its growth pattern. For observed trees that were approximately 20 years old, when grown on unpatented 'Nemaguard' rootstock, the height of the trees were approximately 15 feet. Further, these same trees had a crown spread of approximately 22 feet.

*Productivity*.—Considered very productive. For trees that are at least 20 years old, with currently acceptable planting densities, approximately 3000 pounds of almonds on average are harvested per acre.

*Regularity of bearing*.—Considered regular for the species. No significant alternate bearing has been observed.

*Fertility*.—Self-sterile. The new variety must be cross pollinated by other almond varieties, including 'Nonpareil' (unpatented), 'Bennett-Hickman' (U.S. Plant Pat. No. 26,083), and 'Monterey' (U.S. Plant Pat. No. 3,483).

*Date of harvest*.—Late September, approximately 3 weeks later than unpatented 'Nonpareil' in a normal (non-drought) year.

Trunk:

*Size*.—Considered large, approximately 50.5 inches in circumference when measured at a distance of about 10 inches above the surface of the earth on trees which are at least 20 years old.

*Bark texture*.—Considered moderately rough.

*Bark color*.—Medium gray (13-A-1).

*Bark lenticels*.—No lenticels visible on the trunk (rhytidome is very developed).

Branches:

*Size*.—Considered large for the species, approximately 24 inches in circumference when measured at a distance of approximately 12 inches above the crotch of a 20 year old tree.

*Surface texture*.—Immature branches — Considered smooth.

*Surface texture*.—Mature branches — Considered rough. As wood becomes older, texture becomes rougher with accumulation of lenticels and later rhytidome.

*Bark color*.—Immature branches — First year wood is olive green (22-F-6).

*Bark color*.—Mature branches — Partly medium gray (13-A-1) and partly reddish-brown (7-J-10).

*Lenticels*.—Number, Size and Shape — Approximately 30 per square inch and 5-6 mm in length, and 1-2 mm in width. Shape linear. Color — Gray (55-A-1).

Leaves:

*Size*.—Considered medium for the species, approximately 90 mm in length; and about 22 mm to about 28 mm in width.

*Leaf shape*.—Considered lanceolate.

*Leaf apex*.—Considered acuminate.

*Leaf base*.—Considered acute to rounded.

*Leaf thickness*.—Considered normal for species.

*Leaf color*.—Upwardly facing surfaces — Moderate yellowish green (23-J-6).

*Leaf color*.—Downwardly facing surfaces — Sage green (23-F-47).

*Leaf marginal form*.—Finely serrated.

*Leaf vein*.—Pinnately veined. Color — Vivid yellowish green (20-I-1).

*Leaf petiole*.—Length: about 21 mm to about 30 mm. Leaf Petiole Thickness — about 1-1.25 mm. Leaf Petiole Color — Vivid yellowish green (20-I-1).

*Leaf stipules*.—Very inconspicuous and predominately absent.

*Leaf arrangement*.—The leaves have alternate phyllotaxy.

Flowers:

*Date of full bloom*.—Approximately February 20.

*Bloom amount*.—Typically 2 flowers per cluster.

*Bloom color*.—Upper and lower petal surfaces are the same. Petal base is light pink (1-G-3) while the majority of the petal is white (1-A-1).

*Flower diameter*.—Average 47.6 mm.

*Flower depth*.—Averages 17.5 mm from the base to the ovary to the tip of the stigma.

*Petals*.—Marginal form — Considered elliptic to obovate with widespread apex notching.

*Petals*.—Length — Average 23.6 mm.

*Petals*.—Width — Average 17.0 mm.

*Petal margin*.—Undulate.

*Petal base*.—Acute to 90 degree angle.

*Petals number*.—Generally 5.

*Sepals*.—Color — Upper surface — pale yellowish green (18-I-6). Lower surface — Strong yellow green (19-J-6) with very deep reddish purple (56-L-7) venation.

*Size of individual sepals*.—Average 8.4 mm. in length and about 4.5 mm in width.

*Sepals shape*.—Deltoid.

*Sepals number*.—Generally 5.

*Sepal margin*.—Entire.

*Sepal apex*.—Tapering to a rounded point.

*Pistil length*.—Average 17.5 mm.

*Anthers color*.—Light yellow (9-I-3).

*Pollen production*.—Abundant.

*Pollen color*.—Goldenrod yellow (10-L-5).

*Stamens*.—Length: About 8 mm. to about 12 mm. Average number of stamens — between 25 and 30 on average.

*Style color*.—Pale greenish yellow (12-K-1).

*Style length*.—About 15.0 mm. to about 20.0 mm.

*Stigma color*.—Pyrite yellow (12-L-3).

*Ovary shape*.—Ovate.

*Ovary color*.—Pale green (18-I-4) with heavy pubescence.

*Pedicel length*.—About 2 mm. to about 4 mm.

*Pedicel width*.—Average 1.5 mm.

*Pedicel color*.—Pale yellow green (18-I-6).

*Flower buds* (*before petals show*).—Diameter: Average 7.0 mm.

*Flower buds* (*before petals show*).—Length: Average 13.7 mm.

*Flower buds shape*.—Considered conic.

*Flower buds color just before opening*.—Pinkish white (49-C-2).

*Fragrance*.—Moderate fragrance that is honey-like.

Crop:

*Bearing*.—On average the nut yield of the new variety is greater than that of the unpatented 'Nonpareil' variety.

*Productivity*.—Considered very productive for trees that are 20 years old.

*Hull texture*.—Pubescent.

*Hull form*.—Considered ovate.

*Hull thickness*.—About 2 mm to about 3 mm.

*Hull color*.—Outer color at splitting: Strong yellow green (18-J-6); suture color at splitting: not observed.

*Dehiscence*.—Opens freely.

*Splitting*.—Complete along suture.

Nut:

*Nut size*.—Generally.—Length: Average 37 mm; Width: Average 20 mm.

*Nut shape*.—Considered ovate. Similar to 'Winters' (U.S. Plant Pat. No. 13,286)/'Monterey' (U.S. Plant Pat. No. 3,483).

*Nut thickness*.—Average 16.5 mm.

*Outer shell*.—Form: Considered flaked and brittle.

*Color*.—Shell color at splitting varies from light tan (11-F-6) to moderate tan (11-H-7).

*Pits*.—Small, scattered and numerous.

*Wing*.—Average protrusion is 3 mm from surface of nut tapering at the base and apex.

Kernel:

*Size*.—Length: Average 26 mm; Width: Average 12 mm.

*Shape*.—Elongated ovate. Similar to 'Winters' (U.S. Plant Pat. No. 13,286)/'Monterey' (U.S. Plant Pat. No. 3,483).

*Kernel thickness*.—Average 8.6 mm at hull splitting.

*Stem scar*.—Not readily apparent.

*Apex*.—Shape: Considered acute.

*Surface texture*.—Heavy Smooth. Slightly ribbed along veins with slight pubescence.

*Pubescence*.—Considered slight.

*Color*.—Skin color at splitting Lt. Cocoa (13-L-9); vein color at splitting Light olive brown (15-H-2).

*Numbers of doubles produced*.—Average is 14.6% which is considered select.

*Kernel flavor*.—Sweet, with excellent impact, good after-taste, and good consistency.

*Keeping quality*.—Considered good.

*Keeping and shipping quality*.—Considered good for the variety.

*Average kernel weight*.—About 1.13 grams average weight per kernel. The 'PY2' variety is resistant to anthracnose.

The present variety may be processed as a whole natural, sliced or diced product, good for natural almond butter and is an excellent natural, salted or roasted nut.

Although this new variety of almond tree possess the described characteristics noted above as a result of the growing conditions prevailing in the Modesto area in the San Joaquin Valley of Central California, it is understood that variations of the usual magnitude and characteristics incident to changes in growing conditions, fertilization, pruning and pest control are to be expected.

What is claimed is:

1. A new and distinct variety of almond tree, named 'PY2', substantially as described and illustrated herein, which produces a greater yield than unpatented 'Nonpareil', and which blooms at approximately the same time as 'Monterey' (U.S. Plant Pat. No. 3,483), is a compatible pollinator with 'Monterey', and is ready for harvest at approximately the same time as 'Monterey'.

* * * * *